United States Patent [19]

van de Moesdijk et al.

[11] Patent Number: 4,745,234
[45] Date of Patent: May 17, 1988

[54] PROCESS FOR THE PREPARATION OF α-β UNSATURATED ALCOHOLS

[75] Inventors: Cornelis G. M. van de Moesdijk, Spaubeek; Marcel A. R. Bosma, Geleen, both of Netherlands

[73] Assignee: Stamicarbon B.V., Geleen, Netherlands

[21] Appl. No.: 86,788

[22] Filed: Aug. 19, 1987

Related U.S. Application Data

[63] Continuation of Ser. No. 911,064, Sep. 24, 1986, abandoned.

[30] Foreign Application Priority Data

Oct. 11, 1985 [NL] Netherlands .................. 8502778

[51] Int. Cl.$^4$ .................................. C07C 29/14
[52] U.S. Cl. ................................... 568/830
[58] Field of Search ........................... 568/830

[56] References Cited

U.S. PATENT DOCUMENTS 3,857,900 12/1974 Wilkinson ................. 568/830
4,247,718 1/1981 Dautzenberg et al. ....... 568/830

Primary Examiner—Werren B. Lone
Attorney, Agent, or Firm—Carl G. Love

[57] ABSTRACT

The invention relates to a process for the preparation of α-β unsaturated alcohols of the formula

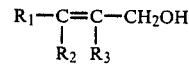

where $R_1$, $R_2$ and $R_3$, which may be equal or different, represent phenyl, optionally substituted with one or more alkyl and/or alkoxy groups, the total number of C atoms of these substituents being at most 5, or hydrogen or an alkyl group with 1-10 C atoms, with at least one of the groups $R_1$, $R_2$ and $R_3$ representing the optionally substituted phenyl group, by hydrogenation in the liquid phase of the aldehyde corresponding with the desired alcohol, this being effected in the presence of a platinum-containing catalyst and of an alkali metal hydroxide and/or an alkali metal alkoxide as promotor, wherein platinum-on-graphite is used as catalyst.

15 Claims, No Drawings

PROCESS FOR THE PREPARATION OF α-β UNSATURATED ALCOHOLS

This is a continuation of application Ser. No. 911,064, filed Sept. 24, 1986, abandoned.

FIELD OF THE INVENTION

The invention relates to a process for the preparation of α-β unsaturated alcohols of the formula

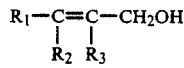

where $R_1$, $R_2$ and $R_3$, which may be equal or different, represent phenyl, optionally substituted with one or more alkyl and/or alkoxi groups, the total number of C atoms of these substituents being at most 5, or hydrogen or an alkyl group with 1-10 C atoms, with at least one of the groups $R_1$, $R_2$ and $R_3$ representing the optionally substituted phenyl group, by hydrogenation in the liquid phase of the aldehyde corresponding with the desired alcohol, this being effected in the presence of a platinum-containing catalyst and of an alkali metal hydroxide and/or an alkali metal alkoxide as promotor. Such alcohols in practice are of importance in the flavours and fragrances industry.

BACKGROUND OF THE INVENTION

A process as described above is known from No. EP-C-4122. This process is suitable for industrial-scale application. The highest efficiencies according to No. EP-C-4122 are achieved at low temperatures, for instance up to 20° C. On a technical scale cooling to such a relatively low temperature of such a strongly exothermic reaction necessitates costly investments as ammonia or nitrite cooling, for instance, is to be applied. If the reaction is carried out at a higher temperature, for instance at 40° C., a simpler cooling system, such as cooling water will suffice, it is true, but then the selectivity of the hydrogenation is found to become substantially lower.

OBJECTS OF THE PRESENT INVENTION

The object of the invention is to provide a process as described in the preamble, is suitable for application on an industrial scale, in which hydrogenation can be effected with high selectivity at elevated temperature.

DESCRIPTION OF THE PRESENT INVENTION

The process according to the invention for the preparation of α-β unsaturated alcohols of the formula

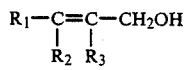

where $R_1$, $R_2$ and $R_3$, which may be equal or different, represent phenyl, optionally substituted with one or more alkyl and/or alkoxy groups, the total number of C atoms of these substituents being at most 5, or hydrogen or an alkyl group with 1-10 C atoms, with at least one of the groups $R_1$, $R_2$ and $R_3$ representing the optionally substituted phenyl group, by hydrogenation in the liquid phase of the aldehyde corresponding with the desired alcohol, this being effected in the presence of a platinum-containing catalyst and of an alkali metal hydroxide and/or an alkali metal alkoxide as promotor, is characterized in that platinum-on-graphite is used as catalyst.

It is noted that in themselves various carriers were already known for platinum-containing catalysts. From U.S. Pat. No. 3,284,517, for instance, kieselguhr, calcium sulphate, carbon and calcium carbonate are known. In No. EP-C-4122, platinum-on-activated-carbon is constantly used. In G.B. Pat. No. 1,123,387, too, preference is given to a platinum-on-activated-carbon catalyst. It was not to be anticipated that replacement of activated carbon by graphite would have such an advantageous effect that the drawback of the state of the art as referred to in the preamble can be overcome.

Examples of aldehydes for which the process according to the invention is particularly suitable are: 3-phenyl-2-propenal(cinnamaldehyde), 2-n-pentyl-3-phenyl-2-propenal, 2-n-hexyl-3-phenyl-2-propenal, 2-methyl-3-phenyl-2-propenal, 2-phenyl-2-pentenal, 2-phenyl-2-propenal and 3-p-methoxyphenyl-2-propenal.

The process according to the invention can be applied in one phase, for instance in isopropyl alcohol. By preference, however, the process according to the invention is applied in a two-phase system of water and a non-water-miscible organic solvent. In such an embodiment of the process according to the invention complete or almost complete conversion can be achieved at low catalyst consumption. In this case various non-water-miscible organic solvents can be used, such as, for instance, benzene, xylenes, cyclopentane, cyclohexane, n-pentane and n-hexane. By preference toluene is used. The ratio of the water to the organic solvent can be varied, for instance between 0.05 and 3 g water per g organic solvent. The amount of organic solvent per g of aldehyde to be converted can be chosen within a wide range, for instance between 0.25 and 20 g, preferably between 0.5 and 5 g organic solvent per g of aldehyde to be converted.

As catalyst, use can be made of the platinum-containing catalysts that are known for hydrogenation, for instance in an amount corresponding with 0.03-5 mg, preferably 0.05-2.5 mg platinum per g of aldehyde to be hydrogenated.

The platinum of the catalyst according to the invention is mounted on a graphite carrier. The weight percentage of platinum, calculated as metal, in itself is not of importance. This percentage may vary from, for instance, 0.1 to 10 wt.%.

The amount of alkali metal hydroxide and/or alkali metal akoxide that is dissolved in the water is, for instance, 0.1-0.7 mol, by preference 0.2-0.5 mol per g water.

In the hydrogenation according to the invention the temperature chosen in principle is not too high, for instance between −5° C. and 60° C. According to the invention it is preferred to use a temperature between 30° C. and 55° C., since at that temperature no special cooling system is required, but the cooling water will suffice. In addition, the reaction proceeds faster than at, for instance, room temperature. If nevertheless, it is preferred to work at a lower temperature, the selectivity that can be reached with the process according to the invention also is higher than that reached with prior art processes.

The hydrogen pressure as such is not critical. A good result is mostly obtained when applying a partial hydrogen pressure of between 500 and 30,000 kPa.

If the hydrogenation is effected in a two-phase system, upon completion the liquid reaction medium can be separated into an organic layer, which contains the desired reaction product, and an aqueous layer, in which the catalyst and the promotor applied are present. This aqueous layer can be used anew in the hydrogenation of the aldehyde. From the organic layer the unsaturated alcohol can be recovered, for instance by distillation, while the organic solvent can be re-used. If a one-phase system is applied, purification of the reaction product can take place by first separating the catalyst by means of filtration and subsequently distilling.

The process according to the invention will be elucidated in the following examples.

EXAMPLES I–XI

A 5-l autoclave provided with a stirrer and a cryostat cooling was charged with 700 g cinnamaldehyde, 467 g toluene, 210 g water, 8.8 g KOH (100%) and 16.8 g catalyst.

The air present was expelled by means of nitrogen. After the desired temperature had been reached, hydrogen was introduced into the autoclave until the desired pressure was reached (Table 1). The set total pressure was maintained throughout the experiment by means of hydrogen.

Upon completion of the experiment the catalyst with the aqueous phase was separated and extracted with toluene. The reaction mixture, which beside cinnamic alcohol also contained phenylpropanol, phenylpropanal as well as unconverted cinnamaldehyde, was analyzed for its composition using gas-liquid chromatography. On the basis of this analysis and the amount of material started from, the conversion and the selectivity could be calculated.

The experiments were varied in weight percentage of platinum in the catalyst, reaction time, temperature and pressure under otherwise identical conditions. These results are presented in Table 1.

TABLE 1

| Example No. | wt. % Pt on graphite | reaction time in hours | temperature in °C. | pressure in kPa | conversion of cinnam- aldehyde % | Selectivity cinnamic alcohol % | phenylpropanal % | phenylpropanol % |
| --- | --- | --- | --- | --- | --- | --- | --- | --- |
| I | 5 | 8 | 20 | 7000 | 98.3 | 99.9 | <0.1 | 0.1 |
| II | 5 | 2 | 35 | 7000 | 99.5 | 94.1 | 0.3 | 5.5 |
| III | 5 | 1.5 | 40 | 7000 | 99.5 | 89.6 | 0.4 | 8.4 |
| IV | 5 | 1 | 50 | 7000 | 99.5 | 87.8 | 0.3 | 8.8 |
| V | 5 | 8 | 20 | 1000 | 98.8 | 97.6 | <0.1 | 2.1 |
| VI | 5 | 4 | 40 | 1000 | 99.6 | 90.2 | 0.2 | 5.1 |
| VII | 3 | 8 | 20 | 1000 | 97.6 | 99.1 | <0.1 | 0.2 |
| VIII | 3 | 5 | 35 | 1000 | 97.8 | 91.2 | 0.2 | 4.9 |
| IX | 3 | 4 | 40 | 1000 | 99.3 | 88.1 | 0.4 | 8.6 |
| X | 3 | 8 | 20 | 7000 | 97.4 | 97.5 | <0.1 | 2.0 |
| XI | 3 | 1.5 | 40 | 7000 | 99.8 | 89.6 | 0.3 | 8.4 |

COMPARATIVE EXAMPLE 1–4

In the same way as described in the above examples, experiments were performed while using a 5 wt.% platinum-on-carbon catalyst. The results of these experiments are presented in Table 2.

TABLE 2

| Example No. | wt. % Pt on activated carbon | reaction time in hours | temperature in °C. | pressure in kPa | conversion of cinnam- aldehyde % | Selectivity cinnamic alcohol % | phenylpropanal % | phenylpropanol % |
| --- | --- | --- | --- | --- | --- | --- | --- | --- |
| 1 | 5 | 7 | 20 | 12000 | 99.4 | 91.6 | 1.0 | 5.8 |
| 2 | 5 | 1.5 | 40 | 12000 | 99.8 | 82.6 | 1.3 | 8.5 |
| 3 | 5 | 7.5 | 20 | 7000 | 98.4 | 91.3 | 1.0 | 6.5 |
| 4 | 5 | 1.5 | 40 | 7000 | 99.6 | 81.8 | 1.4 | 11.2 |

We claim:

1. A process for preparing an α-β unsaturated alcohol having the formula

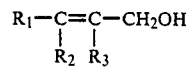

where $R_1$, $R_2$ and $R_3$, independent of one another, represent phenyl, substituted phenyl having one or more alkyl and/or alkoxy groups wherein the total number of carbon atoms of the substituents is at most 5, or hydrogen or a 1–10 carbon atom alkyl group, wherein at least one of $R_1$, $R_2$, and $R_3$ represents substituted phenyl, comprising:
hydrogenating, in the liquid phase, the aldehyde corresponding with the desired alcohol in the presence of a platinum-on-graphite catalyst and a promoter at a partial hydrogen pressure of at least 500 kPa at a temperature from about −5° C. to about 60° C.

2. A process according to claim 1 wherein in said process said promoter is an alkali metal hydroxide, an alkali metal alkoxide, or a combination of an alkali metal hydroxide and an alkali metal alkoxide.

3. Process according to claim 2, wherein the process is carried out in a two-phase system consisting of water and a non-water-miscible organic solvent.

4. Process according to claim 3, characterized in that toluene is used as organic solvent.

5. Process according to claim 2, wherein the catalyst contains 0.1–10 wt.% platinum, calculated as metal.

6. Process according to claim 2, wherein the reaction is carried out at a temperature between 30° and 55° C.

7. Process according to claim 2, wherein as starting material use is made of 3-phenyl-3-propenal, 2-n-pentyl-3-phenyl-2-propenal, 2-n-hexyl-3-phenyl-2-propenal, 2-methyl-3-phenyl-2-propenal, 2-phenyl-2-pentenal, 2-phenyl-2-propenal and 3-p-methoxyphenyl-2-propenal.

8. A process according to claim 2, wherein said process the amount of said catalyst present is about 0.03 to 5 milligrams of platinum per gram of aldehyde to be hydrogenated.

9. A process according to claim 2, wherein said process is conducted at a pressure up to 30,000 kPa.

10. A process for preparing an α-β unsaturated alcohol having the formula

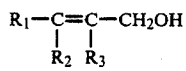

where $R_1$, $R_2$ and R3, independent of one another, represent phenyl, substituted phenyl having one or more alkyl and/or alkoxy groups wherein the total number of carbon atoms of such substituents is at most 5, or hydrogen or an alkyl group having 1–10 carbon atoms, wherein at least one of $R_1$, $R_2$, and R represents substituted phenyl, comprising:
hydrogenating, in the liquid phase, the aldehyde corresponding with the desired alcohol in the presence of a platinum-on-graphite catalyst and a promoter at a partial hydrogen pressure of at least 500 kPa to about 30,000 kPa at a temperature from about 30° C. to about 55° C.

11. A process according to claim 10 wherein in said process said promoter is an alkali metal hydroxide, an alkali metal alkoxide or a combination of an alkali metal hydroxide and an alkali metal alkoxide.

12. A process according to claim 11, wherein said process is conducted in a two-phase system consisting of water and a non-water miscible organic solvent.

13. A process according to claim 12, wherein in said process said promoter is dissolved in said water phase in an amount ranging from 0.01–0.7 mol per gram of water.

14. A process according to claim 12, wherein in said process the amount of said organic solvent per gram of aldehyde being hydrogenated ranges between 0.25 and 20 grams of organic solvent per gram of aldehyde.

15. A process according to claim 12, wherein in said process the amount of said catalyst is about 0.03–5 milligrams of said catalyst per gram of said aldehyde being hydrogenated.

* * * * *